United States Patent [19]

Jackson et al.

[11] Patent Number: 5,753,829
[45] Date of Patent: May 19, 1998

[54] SAMPLING DEVICE

[75] Inventors: Lawrence D.A. Jackson, Guelph; Jan W. Merks, Coquitlam, both of Canada

[73] Assignee: Lawjack Machinery Inc., Guelph, Canada

[21] Appl. No.: 738,743

[22] Filed: Oct. 28, 1996

[51] Int. Cl.$^6$ .................................................. G01N 1/00
[52] U.S. Cl. ............................... 73/863.53; 73/863.56
[58] Field of Search ............. 73/863.41, 863.51–863.56, 73/863.58, 863.44, 863.45

[56] References Cited

U.S. PATENT DOCUMENTS

| 3,464,272 | 9/1969 | Griffith et al. ...................... 73/863.54 |
| 3,555,911 | 1/1971 | Cordell et al. ...................... 73/863.44 |

FOREIGN PATENT DOCUMENTS

| 781 251 | 4/1968 | Canada . | |
| 977578 | 11/1975 | Canada . | |
| 712330 | 10/1941 | Germany | .............. 73/863.54 |
| 2041355 | 3/1972 | Germany | .............. 73/863.55 |

*Primary Examiner*—Robert Raevis
*Attorney, Agent, or Firm*—Townsend and Townsend and Crew LLP

[57] ABSTRACT

A sampling device selects pairs of interleaving samples of slurry flows and is suitable for determining the precision of a measurement protocol and to test the measurement procedure for bias. The device comprises a sample cutter pivoted to move in one direction and in the other direction across a stream of material. A slot is provided in the sample cutter to collect a sample volume from the stream of material as the sample cutter moves across the stream of material. A transfer hopper is positioned to receive the sample volume as the sample cutter moves across the stream and a tilt chute is positioned beneath the hopper movable to divert sample volumes into a first sample container or a second sample container. A mechanism positions the tilt chute over the first sample container and moves the sample cutter in the one direction across the stream of material so a first sample volume is collected in the first sample container and then to position the tilt chute over the second sample container and move the sample cutter in the opposite direction across the stream of material so a second sample volume is collected in the second sample container.

12 Claims, 2 Drawing Sheets

5,753,829

SAMPLING DEVICE

TECHNICAL FIELD

The present invention relates to a sampling device for selecting a pair of interleaving samples of slurry flows at, for example, mineral processing plants. More specifically the present invention relates to a sampling device suitable for determining the precision of a measurement protocol and to test the measurement procedure for bias.

BACKGROUND ART

Estimating precision and testing for bias as disclosed by J. W. Merks on page 214 of his book entitled "Sampling and Weighing of Bulk Solids", published 1985, generally are based on a "statistical comparison of paired measurements in system samples and reference samples". Most present day sampling devices for sampling slurries and other streams of material select unbiased samples for analysis. In Canadian patent No. 782,251 is disclosed a method of obtaining a sample from a pulp stream by reciprocating a sampler transversely of the stream to obtain a sample representative of the stream flowing past the point at which the sampler is introduced. However, the concept of selecting pairs of interleaving samples to estimate the precision of a measurement protocol and to test the measurement procedure for bias has not presently had equipment designed specifically for such purpose.

It is an aim of the present invention to provide a method of sampling a slurry flow and a sampling device for routinely selecting a pair of interleaving samples of a slurry flow such that the sample in one container consists of all odd-numbered sample volumes and the sample in the other container consists of all even-numbered sample volumes with the objective of estimating the precision of a measurement protocol. Testing for bias by comparing pairs of interleaving samples against reference samples does not form part of the present application.

DISCLOSURE OF INVENTION

The present invention provides a method of sampling a stream of material comprising the steps of: moving a sample cutter in one direction transversely across the stream of material to select a first sample volume in a receiving slot in the sample cutter, diverting the first sample volume to a first sample container, moving the sample cutter in the opposite direction transversely across the stream of material to select a second sample volume in the receiving slot, diverting the second sample volume to a second sample container, and repeating the steps of moving the sample cutter at predetermined intervals to divert first sample volumes into the first sample container as the sample cutter moves in the one direction and to divert second sample volumes into the second sample container as the sample cutter moves in the other direction.

The present invention also provides a sampling device for sampling a stream of material comprising: a sample cutter pivoted to move in one direction and in the other direction transversely across the stream of material, a slot in the sample cutter to collect a sample volume from the stream of material as the sample cutter moves across the stream of material, a transfer hopper positioned to receive the sample volume from the sample cutter as it moves across the stream, a tilt chute beneath the hopper movable to divert sample volumes into a first sample container or a second sample container, and mechanism to position the tilt chute over the first sample container and move the sample cutter in the one direction across the stream of material so a first sample volume is collected in the first sample container and then to position the tilt chute over the second sample container and move the sample cutter in the opposite direction across the stream of material so a second sample volume is collected in the second sample container.

BRIEF DESCRIPTION OF DRAWINGS

In drawings which illustrate embodiments of the present invention.

BEST MODE FOR CARRYING OUT THE INVENTION

Figure 1:
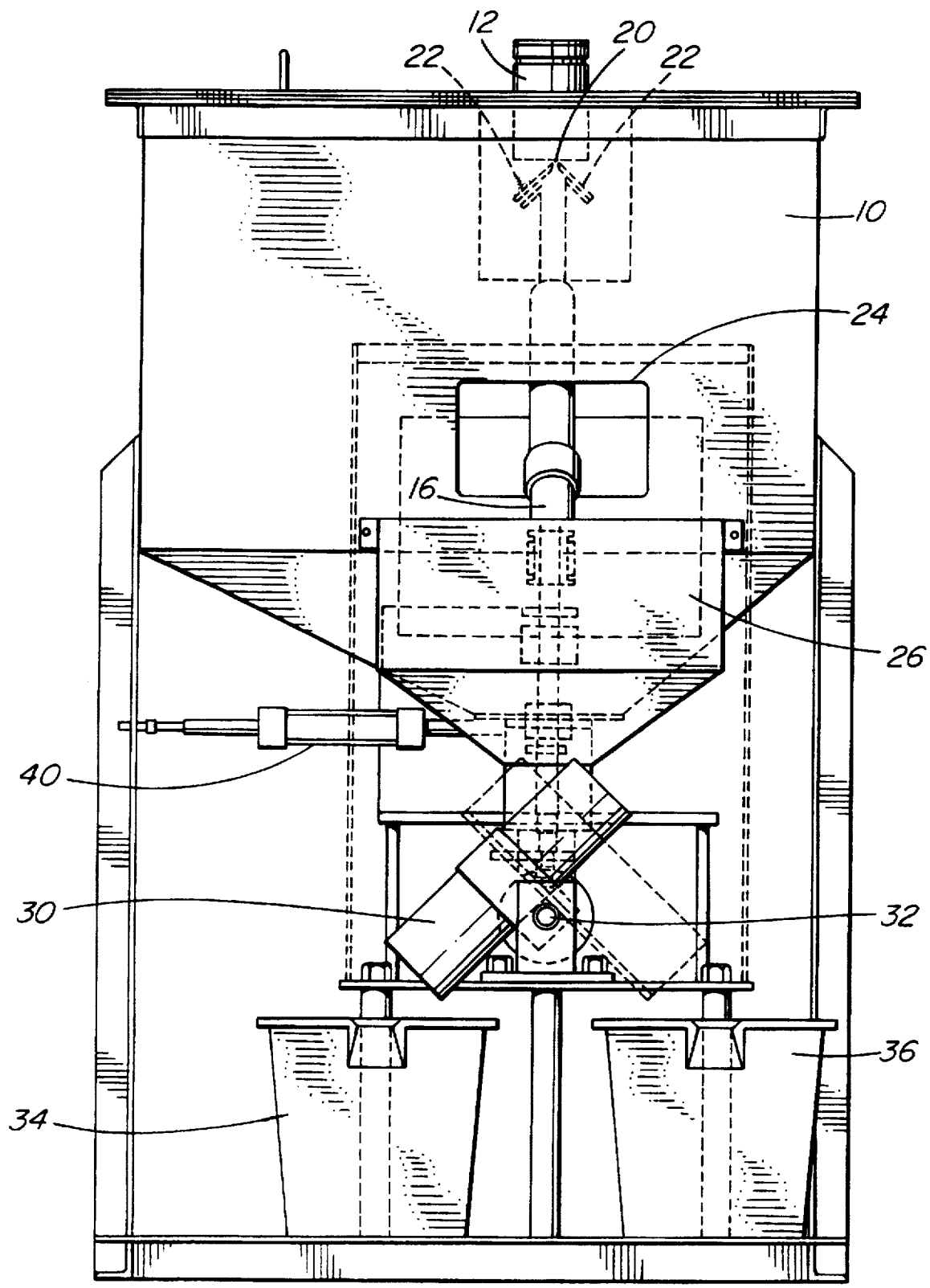
FIG. 1 is a front view showing one embodiment of a sampling device according to the present invention.
Figure 2:
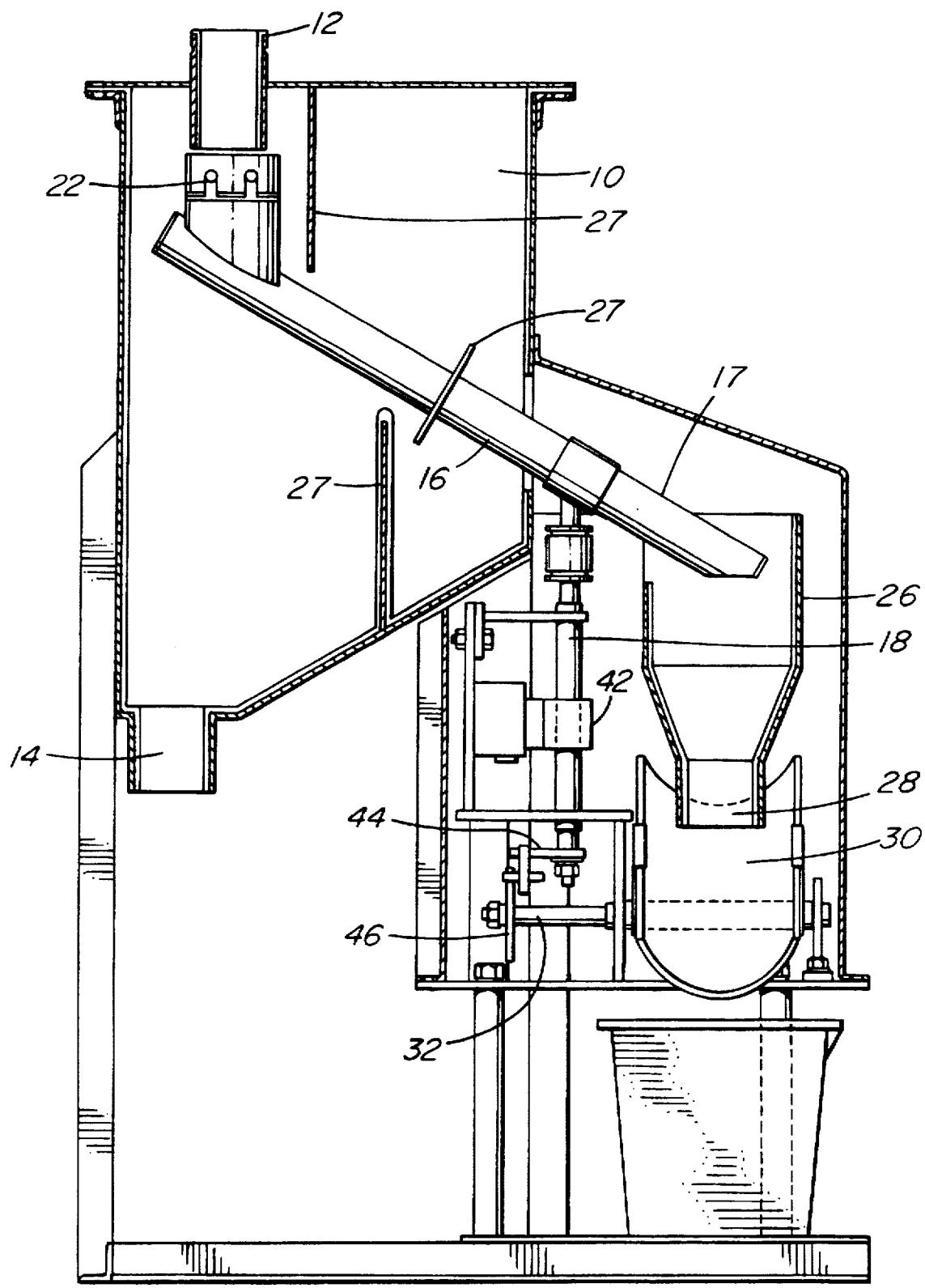
FIG. 2 is a side view, partly in section, showing the sampling device of FIG. 1.

Referring now to the drawings, a sampler chamber 10 has a sample inlet pipe 12 directed downwards for a stream of material such as a slurry to flow downward. The sampler chamber 10 has a sample outlet 14 which permits the slurry reject to be returned to the main slurry flow. A sloped sample cutter 16 with an integral chute 17 is positioned in the sampler chamber 10 and is mounted on a vertical pivot shaft 18 which permits rotational movement of the sample cutter 16 in one direction from left to right and in the opposition direction from right to left transversely across the stream of material flowing from the inlet pipe 12. A slot 20 extends vertically up from the sample cutter 16, the slot 20 is longer than the inlet pipe 12, thus when the sweep pipe 16 moves across the stream of material a complete sample volume of the stream of material is taken. The slot 20 is tapered towards the centre of rotation of the sample cutter 16. In order to permit adjustment of the width of the slot 20, sample cutter blades 22 are provided on each side of the slot. These blades 22 deflect the stream away from the sample cutter 16.

The sample cutter 16 passes through an opening slot 24 in the side of the sampler chamber 10 and extends beyond the pivot shaft 18 to a sample transfer hopper 26. Baffles 27 are provided to prevent splashing from the inlet pipe into the transfer hopper 26. This sample transfer hopper 26 receives a sample from the stream of material through the sample cutter 16 regardless of the location of the sample cutter 16 as it rotates backward and forward beneath the stream of material. Underneath the transfer hopper 26 is an exit 28 which leads to a tilt chute 30 pivoted on a tilt shaft 32. The tilt chute 30 is movable from a first position to a second position to deposit the sample volume into either a first sample container 34 or a second sample container 36 as illustrated in FIG. 1.

The mechanism for operating the sampling device links the pivot shaft 18 to the tilt shaft 32. A double acting pneumatic cylinder 40 has a piston rod connected to a pivot shaft lever arm 42 which rotates the pivot shaft 18 to move the sample cutter 16 either from left to right or from right to left so that a sample of the stream of material may be taken in both directions. At the same time the pivot shaft 18 is connected at its base to a pivot pinion 44 linked to a tilt pinion 46 on the end of the tilt shaft 32 to rotate the tilt shaft and thus move the tilt chute 30 from the first position wherein a sample volume is deposited in the first sampling container 34 to the second position wherein a sample volume is deposited in the second sample container 36.

In operation, when a first sample volume is taken, the piston rod from the pneumatic cylinder 40 moves at a predetermined speed to rotate the pivot shaft 18. The speed of rotation is controlled by varying the air flow or the air pressure or a combination of both to the cylinder. The speed of rotation is constant from sweep to sweep. At the start of a sample sweep, the sample cutter 16 is well to the right in the sampler chamber 10 and as the pivot shaft 18 commences to rotate, the pivot pinion 44 and tilt pinion 46 move so that the tilt chute 30 tilts to deflect a first sample volume to the first sample container 34. The pivot shaft 18 continues to rotate, moving the sample cutter 16 from right to left as seen in FIG. 1. As the slot 20 passes under the stream of material a first sample volume enters the sample cutter 16, passes through the integral chute 17 to the transfer hopper 26 and onto the tilt chute 30 to enter the first sample container 34. The sample cutter 16 continues moving beyond the inlet pipe 12 to stop at the side of the sampler chamber 10.

The sample cutter 16 stops after a first sweep for a predetermined amount of time sufficient to ensure that all of the sample volume drains into the first sample container 34. Then after a predetermined time the second sweep occurs and the reverse action takes place. First of all, as movement of the sample cutter 16 commences moving from left to right, the tilt chute 30 tilts so that the second sample volume enters the second sample container 36. The sample cutter 16 continues to move across the stream of material flowing from the inlet pipe 12 and moves to the other side of the sampler chamber 10. All of the sample volume then passes through the sample cutter 16, the transfer hopper 26 and the tilt chute 30 to enter the second sampler container 36.

In a preferred embodiment, sweeps occur approximately every ten minutes. All the sample volumes taken from the sweep moving from right to left are collected in the first sample container 34 and all the sample volumes collected when the sweep moves from left to right are collected in the second sample container 36. Thus, precision estimates can be obtained from test results for samples from the first sample container 34 and the second sample container 36, and tests for bias can be carried out by comparing test results for samples from the first sample container 34 and the second sample container 36 with test results for reference samples.

The size of the slot 20, the speed of the sample cutter 16 moving from side to side and the time between each sweep is determined by the type of sampling to be conducted. However, variations in all of these may be achieved.

Whereas one embodiment of a mechanism to move the sample cutter 16 and the tilt chute 30 has been disclosed. It will be apparent other types of mechanisms may be incorporated provided that the tilt chute 30 be in position to direct the sample into the appropriate container and remain directed to that container for a sufficient length of time to ensure that no late drips of a sample contaminate the other container.

Various changes may be made to the embodiments shown herein without departing from the scope of the present invention which is limited only by the following claims.

The embodiments of the present invention in which an exclusive property or privilege is claimed are defined as follows:

1. A method of sampling a stream of material, comprising the steps of:
   moving a sample cutter in one direction transversely across the stream of material to select a first sample volume in a receiving slot in the sample cutter;
   diverting the first sample volume to a first sample container;
   moving the sample cutter in the opposite direction transversely across the stream of material to select a second sample volume in the receiving slot;
   diverting the second sample volume to a second sample container, and
   repeating the steps of moving the sample cutter at predetermined intervals to divert first sample volumes into the first sample container as the sample cutter moves in the one direction and divert second sample volumes into the second sample container as the sample cutter moves in the other direction.

2. The method of sampling a stream of material according to claim 1 wherein the sample cutter is in the form of a pipe sloped at an angle and is pivoted about a vertical axis.

3. The method of sampling a stream of material according to claim 1 wherein the first and second sample volumes are diverted to a transfer hopper and wherein a tilt chute is positioned under the hopper tilting from the first sample container to the second sample container being synchronized with moving the sample cutter.

4. The method of sampling a stream of material according to claim 1 wherein the speed of movement of the sample cutter is constant in both directions when the first sample volume and the second sample volume are received in the receiving slot.

5. The method of sampling a stream of material according to claim 1 wherein the stream of material flows downwards.

6. A sampling device for sampling a stream of material comprising:
   a sample cutter pivoted to move in one direction and in the other direction transversely across the stream of material;
   a slot in the sample cutter to collect a sample volume from the stream of material as the sample cutter moves across the stream of material;
   a transfer hopper positioned to receive the sample volume from the sample cutter as it moves across the stream;
   a tilt chute beneath the hopper movable to divert sample volumes into a first sample container or a second sample container, and
   mechanism to position the tilt chute over the first sample container and move the sample cutter in the one direction across the stream of material so a first sample volume is collected in the first sample container and then to position the tilt chute over the second sample container and move the sample cutter in the opposite direction across the stream of material so a second sample volume is collected in the second sample container.

7. A sampling device according to claim 6 wherein the sample cutter in the form of a pipe sloped at an angle and is pivoted about a vertical axis.

8. The sampling device according to claim 6 wherein the stream of material flows downward from an inlet pipe into a sample chamber with a sample outlet at the base thereof.

9. The sampling device according to claim 7 wherein the slot has angled deflector blades on each side and is tapered towards the vertical axis.

10. The sampling device according to claim 7 wherein the sample cutter pivots on a vertical pivot shaft rotating in bearings and has linkage to a pneumatic cylinder with further linkage to move the tilt chute before each sweep.

11. The sampling device according to claim 6 wherein the sample cutter moves at the same speed and rate in the one direction and in the opposite direction.

12. The sampling device according to claim 10 wherein the speed of movement for the sample cutter is controlled by air pressure and air flow to the pneumatic cylinder.

* * * * *